United States Patent [19]

Arsura et al.

[11] 3,982,931
[45] Sept. 28, 1976

[54] N,N-DI-SEC.BUTYL-BENZAMIDE HERBICIDES

[75] Inventors: Emilio Arsura, Milan; Agostino Baruffini; Franco Gialdi, both of Pavia; Giovanni Pellegrini, Milan; Riccardo Ponci, Pavia; Pietro Scrivani, Milan, all of Italy

[73] Assignee: Montedison S.p.A., Milan, Italy

[22] Filed: Apr. 9, 1974

[21] Appl. No.: 459,263

Related U.S. Application Data

[62] Division of Ser. No. 774,475, Nov. 8, 1968, Pat. No. 3,835,189.

[30] Foreign Application Priority Data

Nov. 9, 1967 Italy .................................. 22494/67
Oct. 8, 1968 Italy ................................ 222207/68

[52] U.S. Cl. .................................................. 71/118
[51] Int. Cl.² ........................................... A01N 9/20
[58] Field of Search ...................................... 71/118

[56] References Cited
UNITED STATES PATENTS

| | | | |
|---|---|---|---|
| 2,412,510 | 12/1946 | Jones .................................... | 71/118 |
| 3,014,965 | 12/1961 | Newcomer et al. ................. | 71/118 X |
| 3,130,205 | 4/1964 | Richter .............................. | 71/118 X |
| 3,301,655 | 1/1967 | Wann et al. ........................... | 71/118 |
| 3,342,859 | 9/1967 | Dorfman et al. ..................... | 260/559 |

*Primary Examiner*—Lewis Gotts
*Assistant Examiner*—Catherine L. Mills
*Attorney, Agent, or Firm*—Herbert L. Lerner

[57] ABSTRACT

Described are compounds of the formula:

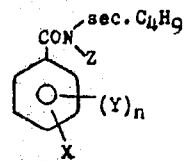

wherein:
 X = Cl, Br, I, $CH_3$;
 Y = H, Cl, Br, I, F, $CH_3$;
 n = 1 or 2,
 Z = alkyl having from 1 to 5 carbon atoms, and when n is 2 only one of X and Y may be $CH_3$. These compounds are useful as selective herbicides.

7 Claims, 1 Drawing Figure

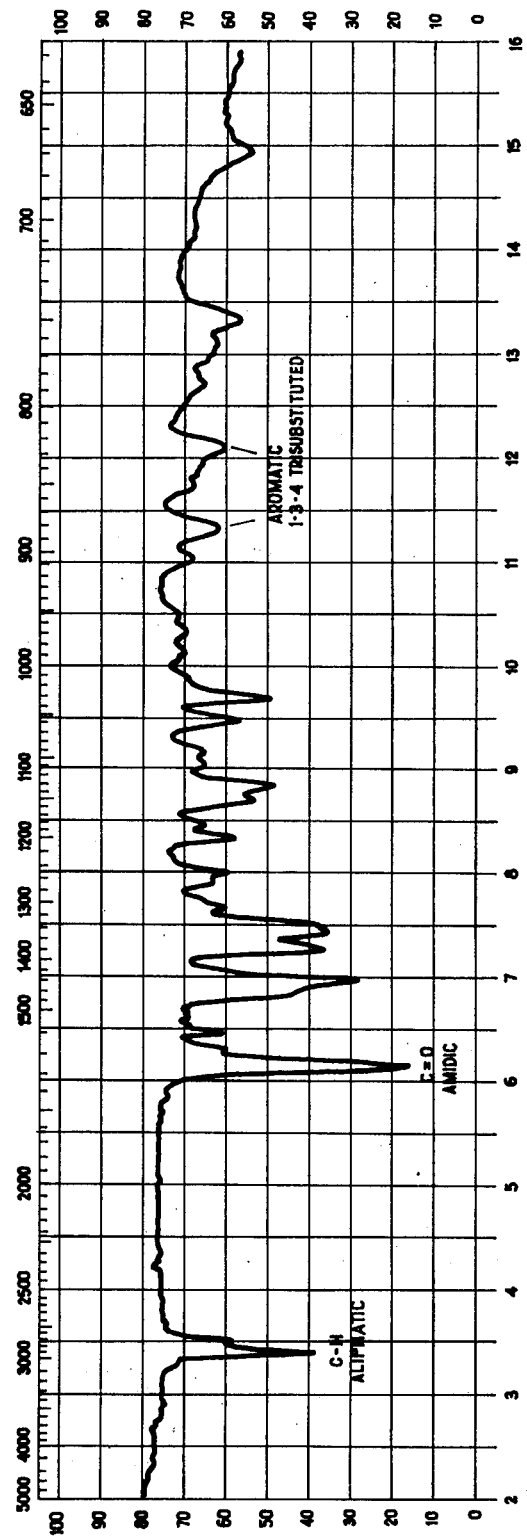

N,N-DI-SEC.BUTYL-BENZAMIDE HERBICIDES

This is a division of application Ser. No. 774,475, filed Nov. 8, 1968 now U.S. Pat. No. 3,835,189 issued Sept. 10, 1974.

Our invention relates to new products having a herbicidal action, the compositions which contain them and their use as herbicides.

For quite a number of years now, research work has been steadily going on throughout the world in the fields of herbicides, in an effort to find products possessing great effectiveness combined with great specificity. For practical purposes, the specificity of action is of extreme importance because it makes possible to selectively exhibit the growth of the infesting plants while leaving the useful plants unharmed.

A number of useful substances have been found for this purpose. However, the necessity for agents having a particular balance of properties and which display specific properties, is still needed. Furthermore, other characteristics are necessary to qualify a satisfactory herbicide. Such characteristics are for instance toxicity for warm-blooded animals, persistence of action, degradability in the soil, etc. Thus it is easily understandable how research in this field will always be required so that for specific applications further technical progress may ensue.

This invention contributes to the technical progress in this field by teaching, in the class of halo(alkyl)-N,N-dialkyl-benzamides, that a particular group of compounds are endowed with a marked specific action associated to a remarkable efficacy and other favorable characteristics. This group of new substances, which constitute an object of this invention, is represented by the formula:

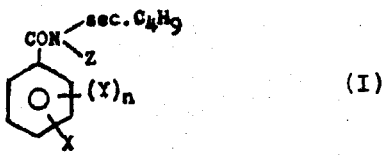

wherein
X = Cl, Br, I, CH$_3$;
Y = H, Cl, Br, I, F, CH$_3$;
n = 1 or 2,
Z = alkyl with 1 to 5 carbon atoms, and when n is 2, only one of X and Y may be CH$_3$.

A further object of this invention are compositions which contain one or more substances of the above formula, in conjunction with means currently in use in the formulation technique, in order to obtain a regular and uniform distribution of relatively small quantities of the herbicidal active ingredients on wide expanses of soil or on the vegetation. The compositions may optionally contain other active ingredients that may develop a complementary action.

In a broad sense, the use of these compounds, no matter what composition contains them nor the technique applied in the treatments, is also within the scope of this invention.

It is well known that the literature shows a herbicidal action of compounds belonging to the class of benzamides (J. Sci. Food Agric. 10 November 1959, pages 577–584 - Pizey and L. Wain).

Furthermore, French Pat. No. 1.466.959, published on Jan. 20, 1967, discloses a class of compounds of the formula:

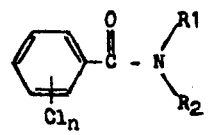

wherein R' is alkyl with 2 to 3 carbon atoms; R$_2$ is hydrogen or alkyl as defined above, and where "n" is a whole number with values from 1 to 3 included. U.S. Pat. No. 3,321,360 claims the use of 3- and 4-bromo-N,N-dialkenyl-benzamides.

The compounds according to the instant invention differ remarkably from those of the above-cited patents and from others of similar classes mentioned in the literature, because of a greater effectiveness or for a greater and different specificity of action which clearly reveals itself in the results obtainable in the selective inhibition of weeds as well as in the external manifestation of change by the plants treated. Thus, of course, one must assume that there is a different mechanism of action.

The observation of such results has definitely been unexpected and surprising since the herbicidal effectiveness in the halo(alkyl)-N,N-dialkyl-benzamides is decreased when the number of carbon atoms of the alkyl groups is > 3, so that, for instance, the halo(alkyl)-N,N-di-n.butyl-benzamides and the halo(alkyl)-N,N-di-n.amyl-benzamides are almost inactive. On the other hand, a notable difference of activity between the halo-N,N-dialkyl-benzamides with alkyls having a number of carbon atoms less than 4 with a linear chain, and the corresponding compounds with a branched chain, is not observed.

Thus it was absolutely unforeseeable that a substantial shift in the values of the herbicidal activity would occur in the halo-N,N-di-sec.butyl-benzamides in comparison to the corresponding halo-N,N-di-n.butyl-benzamides.

The N-sec.butyl-N-alkyl-benzamides of formula (I) can be easily prepared by using the known processes for the preparation of the benzamides. They can be prepared for instance by reacting the chlorides of the halo(alkyl)benzoic acids of the formula:

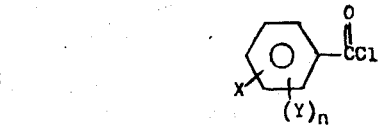

(wherein X, Y and n have the above-described meaning) with di-sec.butylamine or with sec.-butyl-alkylamine.

The halobenzoic acids forming intermediates for the preparation of the compounds according to this invention are known and their preparation is found easily in the literature.

We cite, for instance:
Rec. Trav. Chim. 51, 98–113 (1932),
Rec. Trav. Chim. 50, 753–92 (1931), Rec. Trav. Chim. 49, 1082–92 (1930);
Acta Acad. Aboensis Math.Phys. 8, (4), (1934);
Monatsh 62, 344–8 (1954);
Russian Patent 44,548
J. Indian Chem. Soc. 19, 487–8 (1942);
J. Indian Chem. Soc. 1955, 4139–40;
Med. Proc. SSSR 10, (4), 11–14 (1956);
French Pat. No. 835,727
J. Chem. Soc. 1951, 1211;
Rec. Trav. Chim. 21, (1902), 383;
J. Chem. Soc. 1901, 4349;
J. Chem. Soc. 1903, 332.

Di-sec.butylamine is known; however, some of the sec.butyl-alkylamines, which are used for preparing some of the compounds according to the invention, are new. In any event the latter are also easily obtained by operating according to Campbell et al. - J. Am. Chem. Soc. 66, 82–84, 1944; to British Pat. Nos. 600,841 and 602,332; J. Bewad-J. Prak. Chem. (2) 63, 197 (1901); M. R. Tiollais - Bull. Soc. Ch. Fr. 960 (1947); A. Fleury-Larsoman - Bull Soc. Ch. Fr. (5), 6, 1576 (1939) etc.

The drawing gives the I.R. spectrum of one 3,4-dichloro-N,N-di-sec.-butyl-benzamide.

The following are examples illustrating the invention. The number designations of the examples are preceded with initials. Included are halo(alkyl)N-sec.butyl-N-alkyl-benzamides which are new compounds, and a few N,N-dialkyl-halobenzamides and a few N,N-dialkylamides not described in literature:

PA 235 2-fluoro-N,N-di-sec.butyl-benzamide b.p. = 106°–107°C at 0.1 mm Hg; calc.C=71.70%, found C=71.55%, calc.H=8.82%, found H=8.57%

PA 272 3-fluoro-N,N-di-sec.butyl-benzamide b.p. = 122°–124°C at 0.6 mm Hg; calc.C=71.70%, found C=71.65%, calc.H=8.82%, found H=8.75%

PA 239 4-fluoro-N,N-di-sec.butyl-benzamide b.p. = 106°–108°C at 0.1 mm Hg; calc.C=71.70%, found C=71.55%, calc.H=8.82%, found H=8.60% calc.F=7.56%, found F=7.65%

PA 213 2-chloro-N,N-di-sec.butyl-benzamide b.p. =115°–117°C at 0.1 mm Hg; calc.C=67.28%, found C=66.99%, calc.=8.28%, found H=8.19%

PA 215 3-chloro-N,N-di-sec.butyl-benzamide b.p. = 145°–146°C at 0.5 mm Hg; calc.C=67.28%, found C=66.92%, calc.H=8.28%, found H=8.12% calc.Cl=13.24%, found Cl=13.37%

PA 530 3-chloro-N,n.butyl,N-sec.butyl-benzamide b.p. = 121°C at 0.05 mm Hg; calc.C=67.28%, found C=67.41%, calc.H=8.28%, found H=8.36%

PA 625 3-chloro-N,N-di-sec.amyl-benzamide b.p. = 130°C at 0.05 mm Hg; calc.C=69.02%, found C=68.83%, calc.H=8.86%, found H=8.82%

PA 222 4-chloro-N,N-di-sec.butyl-benzamide b.p. = 123°–124°C at 0.2 mm Hg; calc.C=67.28%, found C=67.00%, calc.H=8.28%, found H=8.04%

PA 432 2-bromo-N,N-di-sec.butyl-benzamide b.p. = 135°C at 0.05 mm Hg; calc.C=57.70%, found C=57.99%, calc.H=7.10%, found H=7.23%

PA 337/3Br 3-bromo-N,N-di-sec.butyl-benzamide b.p. = 153°–154°C at 0.05 mm Hg; calc.C=57.70%, found C=57.79%, calc.H=7.10%, found H=7.28%

PA 525 3-bromo-N,n.butyl-N-sec.butyl-benzamide b.p. = 138°–139°C at 0.05 mm Hg; calc.C=57.70%, found C=57.74%, calc.H=7.10%, found H=7.07%

PA 523 3-bromo-N,N-di-sec.amyl-benzamide b.p. 126°–127°C at 0.05 mm Hg; calc.C=60.00%, found C=59.74%, calc.H=7.70%, found H=7.58%

PA 238 4-bromo-N,N-di-sec.butyl-benzamide b.p. 135°–136°C at 0.1 mm Hg; calc. C=57.70%, found C=57.51%, calc.H=7.10%, found H=7.13%

PA 494 2-iodo-N,N-di-sec.butyl-benzamide b.p. = 147–148°C at 0.1 mm Hg; calc.C=50.15%, found C=50.41%, calc.H=6.17%, found H=6.33%

PA 491 3-iodo-N,N-di-sec.butyl-benzamide b.p. = 141°C at 0.05 mm Hg; calc.C=50.15%, found C=49.92%, calc.H=6.17%, found H=5.96%

PA 287 4-iodo-N,N-di-sec.butyl-benzamide b.p. = 147°C at 0.05 mm Hg; calc.C=50.15%, found C=50.19%, calc.H=6.17%, found H=6.17%

PA 336 2,3-dichloro-N,N-di-sec.butyl-benzamide m.p. = 68°–69°C - crystals from hexane; calc.C=59.61%, found C=59.54%, calc.H=7.00%, found H=6.85%

PA 214 2,4-dichloro-N,N-di-sec.butyl-benzamide m.p. = 73°–75°C - crystals from ligroin; calc.C=59.61%, found C=59.67%, calc.H=7.00%, found H=7.03%

PA 412 2,5-dichloro-N,N-di-sec.butyl-benzamide m.p. = 99°–100°C - crystals from ethanol/$H_2O$; calc.C=59.61%, found C=59.56%, calc.H=7.00%, found H=6.79%

PA 227 2,6-dichloro-N,N-di-sec.butyl-benzamide m.p. = 77°–79°C from ligroin; calc.C=59.61%, found C=59.73%, calc. H=7.00%, found H=7.00%

PA 106 3,4-dichloro-N,N-di-sec.butyl-benzamide crystals: b.p. (in the state of overmelting) = 144°–145°C at 0.1 mm Hg; calc.C=59.61%, found C=59.49%, calc.H=7.00%, found H=6.82% calc.Cl=23.46%, found Cl=23.35%, $n_D^{20}$ = 1,531 (I.R. spectrum in drawing)

PA 562 3,4-dichloro-N-n.propyl,N-sec.butyl-benzamide b.p. = 130°–131°C at 0.05 mm Hg; calc.C=58.34%, found C=58.43%, calc.H=6.65%, found H=6.74%

PA 571 3,4-dichloro-N-isopropyl,N-sec.butyl-benzamide b.p. = 116°C at 0.05 mm Hg; calc.C=58.34%, found C=58.60%, calc.H=6.64%, found H=6.70%

PA 631 3,4-dichloro-N-ethyl,N-sec.butyl-benzamide b.p. = 127°–128°C at 0.05 mm Hg; calc. C=56.94%, found C=57.06%, calc.H=6.25%, found H=6.19%

PA 514 3,4-dichloro-N-n.butyl,N-sec.butyl-benzamide b.p. = 139°–140°C at 0.03 mm Hg; calc.C=59.61%, found C=59.46%, calc.H=7.00%, found H=6.86%

PA 566 3,4-dichloro-N-isobutyl,N-sec.butyl-benzamide b.p. = 133°–134°C at 0.05 mm Hg; calc.C=59.61%, found C=59.53%; calc.H=7.00%, found H=6.66%

PA 623 3,4-dichloro-N,N-di-sec.amyl-benzamide b.p. = 154°C at 0.05 mm Hg; calc.C=61.82%, found C=61.82%, calc.H=7.63%, found H=7.59%

PA 634 3,4-dichloro-N-sec.amyl,N-sec.butyl-benzamide b.p. = 141°–142°C at 0.1 mm Hg; calc.C=60.76%, found C=60.49%, calc.H=7.33%, found H=7.19%

PA 234 3,5-dichloro-N,N-di-sec.butyl-benzamide m.p. = 122°–123°C, crystals from ethanol; calc.C=59.61%, found C=59.86%, calc.H=7.00%, found H=7.03%

PA 538 3,5-dichloro-N,n.butyl,N-sec.butyl-benzamide m.p. = 57°–59°C, crystals from ligroin; calc.C=59.61%, found C=59.63%, calc.H=7.00%, found H=6.98%

PA 537 3,5-dichloro-N,N-di-sec.amyl-benzamide m.p. = 71°–73°C, crystals from hexane; calc.C=61.82%, found C=62.07%, calc. H=7.63%, found H=7.63%

PA 484 3,4-dibromo-N,N-di-sec.butyl-benzamide b.p. = 160°–161°C at 0.05 mm Hg; calc.C=46.06%, found C=46.35%, calc.H=5.41%, found H=5.29%

PA 606 3,5-dibromo-N,N-di-sec.butyl-benzamide m.p. = 118°–120°C, crystals from petroleum ether; calc.C=46.06%, found C=46.12%, calc.H=5.41%, found H=5.24%

PA 569 3,5-diiodo-N,N-di-sec.butyl-benzamide m.p. = 119°–121°C, crystals from ethanol/$H_2O$; calc.C=37.14%, found C=37.16%, calc.H=4.36%, found H=4.37% calc.I=52.32%, found I=52.07%.

PA 504 2-bromo,5-chloro-N,N-di-sec.butyl-benzamide m.p. = 104°–105°C, crystals from ligroin; calc.C=51.97%, found C=51.88%, calc.H=6.10%, found H=6.01%

PA 489 3-bromo,4-chloro-N,N-di-sec.butyl-benzamide b.p. = 154°–155°C at 0.1 mm Hg; calc.C=51.97%, found C=52.10%, calc.H=6.10%, found H=6.39%

PA 626 3-bromo,5-chloro-N,N-di-sec.butyl-benzamide m.p. = 118°–120°C, crystals from methanol/$H_2O$; calc.C=51.97%, found C=52.00%, calc.H=6.10%, found H=6.08%

PA 518 3-bromo,4-fluoro-N,N-di-sec.butyl-benzamide b.p. = 129°C at 0.05 mm Hg; calc.C=54.55%, found C=54.55%, calc.H=6.41%, found H=6.31%

PA 614 4-chloro,3-iodo-N,N-di-sec.butyl-benzamide b.p. = 157°C at 0.1 mm Hg; calc.C=45.76%, found C=45.66%, calc.H=5.38%, found H=5.57%

PA 619 3-iodo,4-bromo-N,N-di-sec.butyl-benzamide m.p. = 84°–86°C, crystals from petroleum ether; calc.C=41.12%, found C=41.13%, calc.H=4.83%, found H=4.83%

PA 300 2,3,5-trichloro-N,N-di-sec.butyl-benzamide m.p. = 111°–112°C, crystals from ethanol; calc.C=53.51%, found C=53.52%, calc.H=5.99%, found H=5.88% calc. Cl=31.59%, found Cl=31.56%

PA 488 2,3,4-trichloro-N,N-di-sec.butyl-benzamide b.p. = 158°–159°C at 0.2 mm Hg; calc.C=53.51%, found C=53.79%, calc.H=5.99%, found H=6.12%

PA 633 2,4,6-trichloro-N,N-di-sec.butyl-benzamide m.p. = 69°–71°C, crystals from methanol/$H_2O$; calc.C=53.51%, found C=53.83%, calc.H=5.99%, found H=5.98%

PA 621 3,4,5-trichloro-N,N-di-sec.butyl-benzamide b.p. = 134°–135°C at 0.1 mm Hg; calc.C=53.51%, found C=53.22%, calc.H=5.99%, found H=5.85%

PA 307 2,3,6-trichloro-N,N-di-sec.butyl-benzamide b.p. = 171°C at 0.05 mm Hg; calc.C=53.51%, found C=53.27%, calc.H=5.99%, found H=5.96%

PA 338 2,4,5-trichloro-N,N-di-sec.butyl-benzamide b.p. = 105°–107°C, crystals from petroleum ether/hexane; calc.C=53.51%, found C=53.31%, calc.H=5.99%, found H=5.92% calc. Cl=31.59%, found Cl=31.03%

PA 510 2,3,5-tribromo-N,N-di-sec.butyl-benzamide m.p. = 116°–117°C, crystals from petroleum ether; calc. C=38.33%, found C=38.70%, calc.H=4.29%, found H=4.32%

PA 502 2,3,5-triiodo-N,N-di-sec.butyl-benzamide m.p. = 114°–116°C, crystals from hexane; calc.C=29.48%, found C=29.59%, calc.H=3.30%, found H=3.13% calc.I=62.30%, found I=62.34%

PA 645 2,5-dichloro,3-iodo-N,N-di-sec.butyl-benzamide m.p. = 124°–126°C, crystals from petroleum ether; calc.C=42.09%, found C=42.25%; calc.H=4.71%, found H=4.65%

PA 445 3-chloro,4-methyl-N,N-di-sec.butyl-benzamide b.p. = 143°–144°C at 0.05 mm Hg; calc.C=68.19%, found C=67.93%, calc.H=8.55%, found H=8.83%

PA 266 3-methyl-N,N-di-sec.butyl-benzamide b.p. = 111°C at 0.1 mm Hg; calc.C=77.68%, found C=77.59%, calc.H=10.19%, found H=10.17%

PA 233 3,4-dimethyl-N,N-di-sec.butyl-benzamide b.p. = 135°–136°C at 0.4 mm Hg; calc.C=78.11%, found C=77.95%, calc.H=10.41%, found H=10.41%

PA 481 3-methyl,4-bromo-N,N-di-sec.butyl-benzamide b.p. = 154°C at 0.05 mm Hg; calc.C=58.90%, found C=58.72,calc.H=7.41%, found H=7.61%

PA 232 3-fluoro,4-methyl-N,N-di-sec.butyl-benzamide b.p. = 126°–127°C at 0.1 mm Hg; calc.C=72.42%, found C=72.18%, calc.H=9.12%, found H=9.21%

PA 480 3,5-dimethyl-N,N-di-sec.butyl-benzamide m.p. = 52.5°C, crystals from ethanol/$H_2O$; calc.C=78.11%, found C=78.23%, calc.H=10.41%, found H=10.35%

PA 237 2-methyl-N,N-di-sec.butyl-benzamide -methyl-N,N-di-sec.butyl-benzamide b.p. = 122°–123°C at 0.2 mm Hg; calc.C=77.68%, found C=77.44%, calc.H=10.19%, found H=9.94%

PA 216 4-methyl-N,N-di-sec.butyl-benzamide b.p. = 107°–108°C at 0.2 mm Hg; calc.C=77.68%, found C=77.78%, calc.H=10.19%, found H=10.08%

Furthermore, we have also surprisingly found that the halo(alkyl)N-sec.butyl-N-alkyl-benzamides comprised in the general formula (I) and obtained according to conventional methods from single halo(alkyl)benzoic acids, optionally in admixture with each other, as well as halo(alkyl)N-sec.butyl-N-alkyl-benzamide mixtures, obtained by amidating mixtures of halo(alkyl)benzoic acids occurring from one single halogenation operation of the benzenic nucleus carried out according to conventional methods may also be used as herbicides. Synergistic effects were observed in the behavior of these mixtures.

Hereunder, in a non-limiting way, are listed the preferred compounds of the invention:

3-chloro-N,N-di-sec.butyl-benzamide; 3-bromo-N,N-di-sec.butyl-benzamide; 3,5-dichloro-N,N-di-sec.butyl-benzamide; 3-bromo, 4-chloro-N,N-di-sec.butyl-benzamide; 3,4-dichloro-N,N-di-sec.butylbenzamide; 3,4-dichloro-N-sec.butyl-N-n-butyl-benzamide; 2,4-dichloro-N,N-di-sec.butyl-benzamide; 2,6-dichloro-N,N-di-sec.butylbenzamide; N,N-di-sec.butyl-amides from a mixture of mono-chlorobenzoic acids (about m.chloro = 83%; o.chloro = 15%; p.chloro = 2%); N,N-di-sec.butylamides from a mixture of trichloro-benzoic acids (about 2,3,6-trichloro = 75%, 2,3,5-trichloro = 25%); 3-iodo-N,N-di-sec.butyl-benzamide; 3-methyl-N,N-di-sec.butyl-benzamide; and 2,3,5-trichloro-N,N-di-sec.butyl-benzamide.

The compounds of this invention are active both in preemergence as well as in post-emergence. The specific characteristic, however, that distinguishes their herbicidal action is the very marked selective action in pre-emergence. In fact, while these compounds exert a considerable and determining phytotoxic action on infesting species, particularly on gramineae, in quantities useful for the herbicidal effect, they leave unharmed important agrarian plants such as for instance: rice, wheat, corn, peas, etc.

The effects on the vegetation manifest themselves substantially through the permanent stopping of the growth of the small plants in the earliest stages of development. The green color of the leaves is intensified, but the growth is completely inhibited and after a certain time the small plants die.

On the other hand, known products of a similar structure impart in the small plants symptoms of suffering from chlorosis and substantially differ from the compounds of this invention in their herbicidal activity either because of a smaller intensity or for lack of selectivity or for a remarkably lower selectivity, particularly with respect to gramineae.

Table 1 following gives recorded demonstrative data of the activity of a number of compounds according to the invention compared to data of known compounds having similar structure, thus exemplifying the subject matter of this application. It is understood that all the data given herein shall have no limiting character on the object of this invention.

These data have been obtained from a treatment carried out by uniformly spreading, by sprinkling, on the soil a quantity of active substance in a hydroacetonic solution corresponding to 6 kg/ha, one day after sowing. This quantity was reduced in the case of some more active products, down to 2 kg.

The data reported refer to the action on the useful plants limited to the products that are more active on the infestants.

The infesting species and the agrarian species have been indicated in Table 1 by letters, as follows:

Infesting species:
A = Amaranthus retroflexus L.
B = Artemisia vulgaris L.
C = Chenopodium album L.
D = Echinocloa crus-galli R.S.
E = Setaria glauca L.
F = Vicia sativa L.

Agrarian species:
G = Avena sativa (oats)
H = Beta vulgaris L. (sugar-beet)
I = Phaseolus vulgaris (bean)
L = Pisum sativum L. (pea)
M = Solanum Lycopersicum L.
N = Triticum vulgare L. (wheat)
O = Zea mais L. (corn)
P = Oryza sativa L. (rice)

Method of evaluation of the results (of tests):
0 = no activity and no difference with respect to the control;
1 slight differences with respect to the control;
2 = activity of a certain degree with partial damages that do not, however, in general, jeopardize the vitality of the small plants;
3 = considerable activity with damages that definitely impair the further development of most of the small plants; an activity degree already useful for practical purposes;
4 = maximum of activity with lack of germination or total containment of the small plants in the emerging stage.

In the case of an intermediate activity between two classes of the scale, both values are recorded with the one which corresponds to the preeminent activity preceding.

TABLE 1

| Mark | Product | kg/ha. | A | B | C | D | E | F |
|---|---|---|---|---|---|---|---|---|
| PA215 | 3,chloro-N,N-disec. butyl.benzamide | 6 | 1–2 | 1–2 | 1–2 | 3 | 3 | 1–2 |
| PA321 | 3,chloro-N,N-diethyl-benzamide | 6 | 1–2 | 2 | 1–2 | 1 | 1 | 1 |
| PA322 | 3,chloro-N,N-di-n.propyl-benzamide | 6 | 1 | 1–2 | 0–1 | 1 | 0–1 | 1–0 |
| PA215 | 2,chloro-N,N-disec.butyl-benzamide | 6 | 2 | 1 | 0–1 | 2–3 | 3 | 0 |
| C | 2,chloro-benzamide | 6 | 2 | 1 | 2 | 0–1 | 0 | 2–3 |
| PA337/3/Br | 3,bromo-N,N-disec. butyl-benzamide | 6 / 4 | 4–3 / 2–3 | 3 / 1 | 4 / 3 | 4 / 4 | 4 / 4 | 1–0 / 1–0 |
| PA396 | 3-bromo-N,N-di-n, butyl-benzamide | 6 | 1 | 1–2 | 0–1 | 0–1 | 0 | 0 |
| PA499 | 3-bromo-N,N-di-allyl-benzamide | 6 / 4 | 4–3 / 2–3 | 3 / 3 | 3 / 2 | 3 / 1 | 3 / 2 | 3 / 1 |
| PA521 | 3-bromo-N,N-di-isobutyl-benzamide | 6 / 6 | 1 / 3–4 | 1 / 3–2 | 1 / 3–2 | 1–2 / 4 | 1–2 / 4 | 0 / 0 |
| PA214 | 2,4-dichloro-N,N-di-ace.butyl-benzamide | 4 / 2 | 2–3 / 1 | 2 / 1 | 1–2 / 1 | 3–4 / 3–2 | 3–4 / 3 | 0 / 0 |
| PA283 | 2,4-dichloro-N,N-di-ethyl-benzamide | 6 | 1 | 2 | 1–2 | 1 | 1 | 1 |
| PA200 | 2,4-dichloro-N,N-di-n-propyl-benzamide | 6 | 3 | 2–3 | 2–3 | 2 | 1 | 0–1 |
| PA281 | 2,4-dichloro-N,N-di-isopropyl-benzamide | 6 | 1–2 | 2 | 0–1 | 0–1 | 0–1 | 0 |
| PA282 | 2,4-dichloro-N,N-di-n.butyl-benzamide | 6 | 2 | 0 | 2 | 1 | 1 | 0–1 |
| PA106 | 3,4-dichloro-N,N-di-sec.butyl- | 6 | 3 | 3 | 3 | 4 | 4 | 0 |

TABLE 1-continued

| | | kg/ha | | | | | | |
|---|---|---|---|---|---|---|---|---|
| | benzamide | 4<br>2 | 2<br>1 | 1-2<br>0-1 | 1-2<br>0-1 | 3-4<br>2 | 3-4<br>3-2 | 0<br>0 |
| PA61 | 3,4-dichloro-N,N-diethyl-benzamide | 6<br>2 | 3-4<br>3 | 3-4<br>3 | 3<br>3 | 3<br>1 | 4-3<br>2 | 3<br>2-3 |
| PA105 | 3,4-dichloro-N,N-di-n.butyl-benzamide | 6<br>3 | 1-2<br>1-0 | 1-2<br>0-1 | 1<br>0-1 | 1<br>0-1 | 2<br>1 | 0-1<br>0 |
| PA259 | 3,4-dichloro-N,N-di-iso-butyl-benzamide | 6 | 1-2 | 2 | 1-2 | 3-2 | 3-2 | 0-1 |
| PA514 | 3,4-dichloro-N-n.butyl-N-sec.butyl-benzamide | 6<br>4<br>2 | 1 | 0-1 | 2 | 3<br>2-3<br>1 | 4-3<br>3<br>2 | 0-1 |
| PA631 | 3,4-dichloro-N-ethyl,N-sec.butyl-benzamide | 6 | 2 | 2 | 3 | 3 | 3 | 0-1 |
| PA325 | 3,4-dichloro-N-ethyl,N-n.butyl-benzamide | 6 | 3 | 2 | 2 | 0-1 | 0-1 | 0 |
| PA234 | 3,5-dichloro-N,N-di-sec.butyl-benzamide | 6<br>4<br>2<br>1<br>0-5 | 2-3<br>2<br>1-2 | 1-2<br>1<br>0-1 | 2<br>2-1<br>1 | 4<br>4<br>4<br>2-3<br>2-1 | 4<br>4<br>4<br>3-4<br>3-2 | 0<br>0<br>0 |
| PA291 | 3,5-dichloro-N,N-diethyl-benzamide | 6<br>4<br>2 | 3-4<br>3<br>2-3 | 4<br>3-4<br>3 | 3<br>3<br>2-3 | 4<br>2-3<br>1-2 | 4<br>3<br>2-3 | 3-4<br>3<br>2-3 |
| PA294 | 3,5-dichloro-N,N-di-n.butyl-benzamide | 6 | 0-1 | 0-1 | 1 | 2 | 3 | 0 |
| PA226 | 3,methyl-N,N-di-sec.butyl-benzamide | 6<br>4<br>2 | 2<br>1-2<br>1-0 | 1-2<br>1-2<br>1 | 1-2<br>1<br>0-1 | 4<br>3<br>2-3 | 4<br>3-4<br>2 | 0<br>0<br>0 |
| PA383 | 3,methyl-N,N-diethyl-benzamide | 6 | 2 | 3 | 2 | 0-1 | 0-1 | 2 |
| PA384 | 3,methyl-N,N-di-n.propyl-benzamide | 6 | 1 | 2 | 2 | 1-2 | 0-1 | 1-2 |
| PA386 | 3,methyl-N,N-di-n.butyl-benzamide | 6 | 3 | 1-2 | 2-3 | 0-1 | 0-1 | 0-1 |
| PA385 | 3,methyl-N,N-di-isopropyl-benzamide | 6 | 1-2 | 2 | 1 | 1-0 | 0-1 | 0-1 |
| PA300 | 2,3,5-trichloro-N,N-di-sec.butyl-benzamide | 6<br>4<br>2<br>1 | 1<br>1<br>1<br>0-1 | 1<br>1<br>1-0<br>0-1 | 1-2<br>1-2<br>1 | 4<br>4-3<br>3-4<br>3 | 4<br>4<br>4-3<br>3-4 | 0<br>0<br>0<br>0 |
| PA303 | 2,3,5-trichloro-N,N-di-n. propyl-benzamide | 6<br>4<br>2<br>1 | 3<br>2-3<br>2-1<br>1 | 1<br>1<br>1<br>1 | 2-1<br>1-2<br>1<br>1 | 4<br>3-4<br>3-2<br>1-2 | 4<br>4-3<br>3<br>1-2 | 0-1<br>0-1<br>0<br>0 |
| PA302 | 2,3,5-trichloro-N,N-di-iso-propyl-benzamide | 6<br>3<br>1 | 2-3<br>2<br>2-1 | 2<br>2<br>1-2 | 3<br>3<br>2 | 4<br>4<br>4-3 | 4<br>4<br>3-4 | 0-1<br>0-1<br>0 |
| PA439 | 3,chloro-benzoic acid | 6 | 0 | 0 | 0 | 0 | 0 | 0 |
| PA577 | 3,bromo-benzoic acid | 6 | 0 | 0 | 0 | 0 | 0 | 0 |
| PA441 | 2,4-dichloro-benzoic acid | 6 | 0 | 0 | 0 | 0 | 0 | 0 |
| Acid | 3,4-dichloro-benzoic acid | 6 | 0 | 0 | 0 | 0 | 0 | 0 |
| PA440 | 3,5-dichloro-benzoic acid | 6 | 0 | 0 | 0 | 0 | 0 | 0 |
| PA304 | 2,3,5-trichloro-benzoic acid | 6 | 1 | 1 | 0 | 0 | 0 | 3 |
| PA442 | 3,methyl-benzoic acid | 6 | 1 | 0 | 0 | 0 | 0 | 0 |

| Mark | Product | kg/ha. | G | H | I | L | M | N | O | P |
|---|---|---|---|---|---|---|---|---|---|---|
| PA215 | 3,chloro-N,N-disec.butyl.benzamide | 6 | 0 | | 0 | | | | 0 | 0 |
| PA321 | 3,chloro-N,N-diethyl-benzamide | 6 | 1 | | 1-0 | 2 | | 2-3 | 0-1 | 2 |
| PA322 | 3,chloro-N,N-di-n.propyl-benzamide | | | | | | | | | |
| PA215 | 2,chloro-N,N-disec.bu- | | | | | | | | | |

TABLE 1-continued

| | | | | | | | | | | |
|---|---|---|---|---|---|---|---|---|---|---|
| | tyl-benzamide | 6 | 0 | | 0 | 0 | | 0 | 0 | |
| C | 2,chloro-benzamide | 6 | | | | | 0–1 | 0–1 | | |
| Pa337/ 3/Hr | 3,bromo-N,N-disec butyl-benzamide | 6 3 | 0 0 | 1 1 | 1 0 | 0 0 | 1–2 1 | 0 0 | 0 0 | 0 |
| PA396 | 3-bromo-N,N-di-n, butyl-benzamide | | | | | | | | | |
| PA499 | 3-bromo-N,N-di-allyl- benzamide | | | | | | | | | |
| PA521 | 3-bromo-N,N-di-isobu- tyl-benzamide | 6 | 0 | | 0 | 0 | | 0 | 0 | |
| PA214 | 2,4-dichloro-N,N-di- sec.butyl-benzamide | | | | | | | | | |
| PA285 | 2,4-dichloro-N,N-di- ethyl-benzamide | | | | | | | | | |
| PA200 | 2,4-dichloro-N,N-di- n-propyl-benzamide | | | | | | | | | |
| PA281 | 2,4-dichloro-N,N-di-isopropyl- benzamide | | | | | | | | | |
| PA282 | 2,4-dichloro-N,N-di-n.butyl- benzamide | | | | | | | | | |
| PA106 | 3,4-dichloro-N,N-di-sec.butyl- benzamide | 6 | 0 | 1 | 0 | 0 | 0 | 0 | 0 | 0 |
| PA61 | 3,4-dichloro-N,N-diethyl-ben- zamide | 6 | 1 | 3–4 | 1 | 1 | 3–4 | 1 | 2 | 3 |
| PA105 | 3,4-dichloro-N,N-di-n.butyl- benzamide | | | | | | | | | |
| PA259 | 3,4-dichloro-N,N-di-iso-butyl- benzamide | | | | | | | | | |
| PA514 | 3,4-dichloro-N-n.butyl-N-sec. butyl-benzamide | 6 3 | 0 0 | 2–3 1–2 | 0 0 | 0 0 | 0 0 | 0 0 | 0 0 | 0 |
| PA631 | 3,4-dichloro-N-ethyl,N-sec. butyl-benzamide | | | | | | | | | |
| PA325 | 3,4-dichloro-N-ethyl,N-n. butyl-benzamide | | | | | | | | | |
| PA234 | 3,5-dichloro-N,N-di-sec.butyl- benzamide | 6 4 2 | 0 0 0 | 1 1 0 | 0 0 0 | 0 0 0 | 1 1 1 | 0 0 0 | 0 0 0 | 0 |
| PA291 | 3,5-dichloro-N,N-diethyl-benza- mide | 6 3 | | | 4 3–4 | 3–4 3 | | 4 4 | 4 4 | 4 |
| PA294 | 3,5-dichloro-N,N-di-n.butyl-ben- zamide | | | | | | | | | |
| PA226 | 3,methyl-N,N-di-sec.butyl-benza- mide | 6 | 0 | | 0 | 0 | | 0 | 0 | |
| PA383 | 3,methyl-N,N-diethyl-benzamide | | | | | | | | | |
| PA384 | 3,methyl-N,N-di-n.propyl-benza- mide | | | | | | | | | |
| PA386 | 3,methyl-N,N-di-n.butyl-benza- mide | | | | | | | | | |
| PA385 | 3,methyl-N,N-di-isopropyl-benza- mide | | | | | | | | | |
| PA | 2,3,5-trichloro-N,N-di- sec.butyl-benzamide | 6 3 | 1 0 | | 0 0 | 0 0 | | 0 0 | 0 0 | 0 0 |
| PA303 | 2,5,5-trichloro-N,N-di- n. propyl-benzamide | 6 3 | 2 1 | | 2 1 | 1 1 | | 2 1 | 4–3 3 | 3 3 |
| PA302 | 2,3,5-trichloro-N,N-di- iso-propyl-benzamide | 6 3 | 2–3 2 | 4–3 3 | 1–0 0–1 | 1 0 | 3 2–3 | 3–2 2 | 3 1–2 | 4–3 |
| PA439 | 3,chloro-benzoic acid | | | | | | | | | |
| PA577 | 3,bromo-benzoic acid | | | | | | | | | |
| PA441 | 2,4-dichloro-benzoic acid | | | | | | | | | |
| Acid | 3,4-dichloro-benzoic acid | | | | | | | | | |

TABLE 1-continued

| PA440 | 3,5-dichloro-benzoic acid |
| --- | --- |
| PA304 | 2,3,5-trichloro-benzoic acid |
| PA442 | 3,methyl-benzoic acid |

From the data recorded on Table 1, it will be seen that in general the herbicidal activity of the halo(alkyl)N,N-dialkyl-benzamides which do not fall within the field of this invention is considerably less intense than that of the compounds according to the invention. It will also be noted that some of the halo-N,N-dialkyl-benzamides, such as for instance: 3,5-dichloro-N,N-diethylbenzamide, 3,5-dichloro-N,N-di-n.propyl-benzamide, 2,3,5-trichloro-N,N-diiso-propylbenzamide (compounds not comprised by the general formula of this invention), have a very diffused herbicidal action and besides are very active, in particular against infesting gramineae, but also exert, however, a phytotoxic action of considerable intensity on useful plants and in particular on useful gramineae.

On the contrary, the phytotoxic action of the products according to this invention, although acting intensely on the infesting graminae, has no effect on the useful gramineae in operational quantities for full effectiveness against the infesting plants.

Also the effects deriving from the phytotoxic action of the compounds put to comparison, as already stated, manifest themselves on the plants in a completely different way.

How a structural variation of a relatively modest extent can lead to such a substantial difference in behavior and effects, is still not clear.

It is also noted that halo(alkyl)N,N-dialkyl-benzamides with an alkyl having 4 carbon atoms, different than sec.butyl, are almost inactive or very much less active compared to the halo(alkyl)N,N-di-sec.butyl-benzamides and the halo(alkyl)N,sec.butyl-N, alkyl-benzamides, so that for practical purposes the first-mentioned compounds cannot be used.

TABLE 2 reports the activity data of other compounds that fall within the class which is the object of this invention. This data has been obtained from tests carried out with the same technique used for the tests of Table 1.

TABLE 2

| MARK: | Product: | kg/ha | A | B | C | D | E | F |
| --- | --- | --- | --- | --- | --- | --- | --- | --- |
| PA215 | 3,chloro-N,N-di-sec.butyl-benzamide | 6 | 1–2 | 1–2 | 1–2 | 3 | 3 | 1–2 |
| PA491 | 3,iodo-N,N-di-sec.butyl-benzamide | 6 | 3–4 | 4 | 3–4 | 4 | 4 | 1 |
| | | 4 | 1–2 | 3 | 2–3 | 4–3 | 4–3 | 0 |
| | | 2 | 1 | 1 | 2 | 3 | 3 | 0 |
| PA337/3/Br | 3,bromo-N,N-di-sec.butyl-benzamide | 6 | 4–3 | 3 | 4 | 4 | 4 | 1–0 |
| | | 4 | 2–3 | 1 | 3 | 4 | 4 | 1–0 |
| | | 2 | 1 | 1–0 | 1 | 2 | 2–3 | 0–1 |
| PA489 | 3,bromo-4,chloro-N,N-di-sec.butyl-benzamide | 6 | 3 | 3 | 2 | 3–4 | 4 | 0–1 |
| | | 4 | 1–2 | 1 | 1–2 | 3–4 | 4–3 | 0 |
| | | 2 | 1 | 0–1 | 1 | 3–2 | 3 | 0 |
| PA106 | 3,4dichloro-N,N-di-sec.butyl benzamide | 6 | 3 | 3 | 3 | 4 | 4 | 0 |
| | | 4 | 2 | 1–2 | 1–2 | 3–4 | 3–4 | 0 |
| | | 2 | 1 | 0–1 | 0–1 | 2 | 3–2 | 0 |
| PA336 | 2,3-dichloro-N,N-di-sec.butyl-benzamide | 6 | 4 | 3 | 4–3 | 4 | 4 | 0 |
| | | 4 | 3–1 | 2 | 3 | 4 | 4 | 0 |
| | | 2 | 2–3 | 1 | 2 | 3–4 | 4–3 | 0 |
| PA214 | 2,4-chloro-N,N-di-sec.butyl-benzamide | 6 | 3–4 | 3–2 | 3–2 | 4 | 4 | 0 |
| | | 4 | 2–3 | 2 | 1–2 | 3–4 | 3–4 | 0 |
| | | 2 | 1 | 1 | 1 | 3–2 | 3 | 0 |
| PA412 | 2,5-dichloro-N,N-di-sec.butyl-benzamide | 6 | 3 | 2 | 2–3 | 4 | 4 | 0 |
| | | 3 | 2 | 1 | 1–2 | 3–4 | 4 | 0 |
| | | 2 | | | | 3 | 3 | |
| | | 1 | | | | 1–2 | 3 | |
| PA227 | 2,6-dichloro-N,N-di-sec.butyl-benzamide | 6 | 4–3 | 2 | 3–4 | 4 | 4 | 0 |
| | | 4 | 3 | 1–2 | 2 | 3 | 3 | 0 |
| | | 2 | 1–2 | 0–1 | 1 | 2 | 2 | 0 |
| PA484 | 3,4-dibromo-N,N-di-sec.butyl-benzamide | 6 | 2–3 | 2–3 | 2 | 3–4 | 4–3 | 0 |
| | | 4 | 1–2 | 1 | 1 | 3 | 3 | 0 |
| PA504 | 2,bromo-5,chloro-N,N-di-sec.-butyl-benzamide | 6 | 2 | 1–2 | 2 | 3–4 | 4 | 0–1 |
| | | 4 | | | | 3 | 3–4 | |
| | | 3 | | | | 2–3 | 3 | |
| | | 2 | | | | 2–3 | 2–3 | |
| PA518 | 3,bromo-4,fluoro-N,N-di-sec.-butyl-benzamide | 6 | 2 | 3 | 3 | 3–4 | 4 | 0 |
| PA619 | 3,iodo-4,bromo-N,N-di-sec.butyl-benzamide | 6 | 0–1 | 0 | 0–1 | 3 | 3 | 0 |

TABLE 2-continued

| | | kg/ha | | | | | | | |
|---|---|---|---|---|---|---|---|---|---|
| PA614 | 3,iodo-4,chloro-N,N-di-sec.butyl-benzamide | 6 | 1 | 0–1 | 1 | 3 | 4–3 | 0 | |
| PA626 | 3,bromo,5-chloro-N,N-di-sec.butyl-benzamide | 6 | 1–2 | 0–1 | 0–1 | 3–4 | 4 | 0 | |
| PA488 | 2,3,4-trichloro-N,N-di-sec.butyl-benzamide | 6<br>4<br>2<br>1 | 3–4<br>1<br>0 | 4–3<br>0–1<br>0 | 3<br>3<br>1–2 | 4<br>4<br>3–4<br>2 | 4<br>4<br>4–3<br>3–2 | 0<br>0<br>0 | |
| PA633 | 2,4,6-trichloro-N,N-di-sec.butyl-benzamide | 6 | 2 | 2–3 | 2–3 | 4 | 4 | 0 | |
| PA621 | 3,4,5-trichloro-N,N-di-sec.butyl-benzamide | 6 | 2 | 2 | 2 | 4 | 4 | 0 | |
| PA525 | 3,bromo-N,n.butyl-N-sec.butyl-benzamide | 6 | 1–2 | 0–1 | 1 | 3 | 3–4 | 0 | |
| PA634 | 3,4-dichloro-N,sec.amyl,N-sec.butyl-benzamide | 6 | 2 | 2 | 1–2 | 3 | 3–4 | 0 | |
| PA566 | 3,4-dichloro-N,isobutyl-N-sec.butyl-benzamide | 6 | 3 | 2–3 | 3 | 4–3 | 4 | 0–1 | |
| PA234 | 3,5-dichloro-N,N-di-sec.butyl-benzamide | 6<br>4<br>2<br>1<br>0.5 | 2–3<br>2<br>1–2 | 1–2<br>1<br>0–1 | 2<br>2–1<br>1 | 4<br>4<br>4<br>2–3<br>2–1 | 4<br>4<br>4<br>3–4<br>3–2 | 0<br>0<br>0 | |
| PA300 | 2,3,5-trichloro-N,N-di-sec.butyl-benzamide | 6<br>4<br>2<br>1 | 1<br>1<br>1<br>0–1 | 1<br>1<br>1–0<br>0–1 | 1–2<br>1–2<br>1<br>0–1 | 4<br>4–3<br>3–4<br>3 | 4<br>4<br>4–3<br>3–4 | 0<br>0<br>0<br>0 | |
| PA338 | 2,4,5-trichloro-N,N-di-sec.butyl-benzamide | 6<br>4<br>2 | 2 | 1–2 | 2 | 3–4<br>3<br>2–3 | 3–4<br>3<br>2–3 | 0–1 | |
| PA514 | 3,4-dichloro-N-sec.butyl,N,n.butyl-benzamide | 6<br>4<br>2 | 1 | 0–1 | 2 | 3<br>2–3<br>1 | 4–3<br>3<br>2 | 0–1 | |
| PA489 | 3,bromo,4-chloro-N,N-di-sec.butyl-benzamide | 6<br>4<br>2 | 3 | 3 | 2 | 3–4<br>3–4<br>3–2 | 4<br>4–3<br>3 | 0–1 | |
| PA445 | 3,chloro,4-methyl,N,N-di-sec.butyl-benzamide | 6<br>4<br>2 | 2<br>1<br>0–1 | 3–4<br>2<br>1 | 4<br>2–3<br>1 | 4<br>3–4<br>3 | 4<br>4–3<br>3–4 | 0–1<br>0<br>0 | |
| PA226 | 3,methyl-N,N-di-sec.butyl-benzamide | 6<br>4<br>2 | 2 | 1–2 | 1–2 | 4<br>3<br>2–3 | 4<br>3–4<br>2 | 0 | |
| PA233 | 3,4-dimethyl-N,N-di-sec.butyl-benzamide | 6<br>4<br>2 | 2–3 | 2 | 2 | 4<br>3<br>2–3 | 4<br>3–4<br>3 | 0 | |
| PA481 | 3,methyl-4,bromo-N,N-di-sec.butyl-benzamide | 6 | 2–1 | 3 | 2–3 | 4–3 | 3–4 | 0–1 | |
| PAK 2 | mixture of trichloro-N,N-di-sec.butyl-bezamides(2,3,6,Cl₃=75%; 2,3,5,Cl₃ = 25%) | 6<br>4<br>2 | 4–3<br>3<br>2–3 | 4<br>3<br>1–2 | 3–4<br>3<br>2 | 4<br>4<br>4–3 | 4<br>4<br>4–3 | 0<br>0<br>0 | |
| PAK 1 | mixture of monochloro-N,N-di-sec.butyl-benzamides (3 Cl=83.1%; 2Cl=14.1%; 4Cl=2%) | 6<br>4<br>2 | 3<br>2<br>0–1 | 3–4<br>2<br>0 | 2–3<br>2<br>0–1 | 3–4<br>3<br>1–2 | 4<br>3<br>1–2 | 0–1<br>0<br>0 | |
| PAK 3 | mixture of dichloro-N,N-di-sec.butyl-benzamides (2,5Cl₂=70%; 2,3-Cl₂=23%; 3,4-Cl₂=7%) | 6<br>4<br>2 | 3<br>3–2<br>2 | 2<br>2<br>1 | 3<br>3–2<br>1–2 | 4<br>4<br>3 | 4<br>4<br>3 | 0<br>0<br>0 | |
| PAK 4 | mixture of trichloro-N,N-di-sec.butyl-benzamides (2,4,5-Cl₃=66%; 2,3,4-Cl₃=33%) | 6<br>4<br>2 | 3–2<br>2<br>1 | 1–2<br>1<br>0–1 | 2<br>1–2<br>0–1 | 4–3<br>4–3<br>3 | 4<br>4<br>3–4 | 0<br>0<br>0 | |

| MARK: | Product: | kg/ha | G | H | I | L | M | N | O | P |
|---|---|---|---|---|---|---|---|---|---|---|
| PA215 | 3,chloro-N,N-di-sec.butyl-benzamide | 6 | 0 | | 0 | | | | | |
| PA491 | 3,iodo-N,N-di-sec.butyl-benzamide | 6<br>3 | 0<br>0 | 1<br>0 | 0<br>0 | 0<br>0 | 1<br>0 | 0<br>0 | 0<br>0 | |
| PA337/<br>/3/Br | 3,bromo-N,N-di-sec.butyl-benzamide | 6<br>3 | 0<br>0 | 1<br>1 | 1<br>0 | 0<br>0 | 1–2<br>1 | 0<br>0 | 0<br>0 | |

TABLE 2-continued

| | | | | | | | | | | | |
|---|---|---|---|---|---|---|---|---|---|---|---|
| PA489 | 3,bromo-4,chloro-N,N-di-sec.butyl-benzamide | 6 | 0 | 1 | 0 | 0 | 1 | 0 | 0 | 0 | |
| | | 3 | 0 | | 0 | 0 | | | 0 | 0 | |
| PA106 | 3,4dichloro-N,N-di-sec.butyl benzamide | 6 | 0 | 1 | 0 | 0 | 0 | 0 | 0 | 0 | |
| PA336 | 2,3-dichloro-N,N-di-sec.butyl-benzamide | 6 | 0 | | 0 | 0 | | | 0 | 0 | |
| PA214 | 2,4-chloro-N,N-di-sec.butyl-benzamide | 6 | 0 | | 0 | 0 | | | 0 | 0 | |
| PA412 | 2,5-dichloro-N,N-di-sec.butyl-benzamide | 6 | 0 | 2 | 0 | 0 | 1 | 0 | 0 | 0 | |
| | | 3 | 0 | 1 | 0 | 0 | 1 | 0 | 0 | | |
| PA227 | 2,6-dichloro-N,N-di-sec.butyl-benzamide | 6 | 0 | 2 | 0 | 0 | 1 | 0 | 0 | 0 | |
| PA484 | 3,4-dibromo-N,N-di-sec.butyl-benzamide | | | | | | | | | | |
| PA504 | 2,bromo-5,chloro-N,N-di-sec.-butyl-benzamide | | | | | | | | | | |
| PA518 | 3,bromo-4,fluoro,N,N-di-sec.-butyl-benzamine | | | | | | | | | | |
| PA619 | 3,iodo-4,bromo-N,N-di-sec.butyl-benzamide | | | | | | | | | | |
| PA614 | 3,iodo-4,chloro-N,N-di-sec.butyl-benzamide | | | | | | | | | | |
| PA626 | 3,bromo,5-chloro,N,N-di-sec.butyl-benzamide | | | | | | | | | | |
| PA488 | 2,3,4-trichloro-N,N-di-sec.butyl-benzamide | 6 | 0 | 1–2 | 0 | 0 | 1 | 0 | 1 | 0 | |
| | | 3 | 0 | 0 | 0 | 0 | 0 | 0 | 0 | | |
| PA633 | 2,4,6-trichloro-N,N-di-sec.butyl-benzamide | | | | | | | | | | |
| PA621 | 3,4,5-trichloro-N,N-di-sec.butyl-benzamide | | | | | | | | | | |
| PA525 | 3,bromo-N,n.butyl-N-sec.butyl-benzamide | | | | | | | | | | |
| PA634 | 3,4-dichloro-N,sec.amyl,N-sec.butyl-benzamide | | | | | | | | | | |
| PA566 | 3,4-dichloro-N,isobutyl-N-sec.butyl-benzamide | | | | | | | | | | |
| PA234 | 3,5-dichloro-N,N-di-sec.butyl-benzamide | 6 | 0 | 1 | 0 | 0 | 1 | 0 | 0 | 0 | |
| | | 4 | 0 | 1 | 0 | 0 | 1 | 0 | 0 | | |
| | | 2 | 0 | 0 | 0 | 0 | 1 | 0 | 0 | | |
| PA300 | 2,3,5-trichloro-N,N-di-sec.butyl-benzamide | 6 | 1 | | 0 | 0 | | 0 | 0 | 0 | |
| | | 3 | 0 | | 0 | 0 | | 0 | 0 | | |
| PA338 | 2,4,5-trichloro-N,N-di-sec.butyl-benzamide | 6 | 0 | 2 | 0 | 0 | 2 | 0 | 0 | 0 | |
| | | 3 | 0 | 1 | 0 | 0 | 1 | 0 | 0 | | |
| PA514 | 3,4-dichloro-N-sec.butyl,N,n.butyl-benzamide | 6 | 0 | 2–3 | 0 | 0 | 0 | 0 | 0 | 0 | |
| | | 3 | 0 | 1–2 | 0 | 0 | 0 | 0 | 0 | | |
| PA489 | 3,bromo,4-chloro,N,N-di-sec.butyl-benzamide | 6 | 0 | 1 | 0 | 0 | 1 | 0 | 0 | 0 | |
| | | 3 | 0 | | 0 | 0 | | 0 | 0 | | |
| PA445 | 3,chloro-4-methyl,N,N-di-sec.butyl-benzamide | 6 | 0 | 1 | 0 | 0 | 0 | 0 | 0 | 0 | |
| | | 3 | 0 | 0 | 0 | 0 | 0 | 0 | 0 | | |
| PA226 | 3,methyl-N,N-di-sec.butyl-benzamide | 6 | 0 | | 0 | 0 | | | 0 | 0 | |
| PA233 | 3,4-dimethyl-N,N-di-sec.butyl-benzamide | 6 | 0 | | 0 | 0 | | 1 | 0 | | |
| | | 3 | 0 | | 0 | 0 | | 0 | 0 | | |
| PA481 | 3,methyl-4,bromo-N,N-di-sec.butyl-benzamide | 6 | 0 | 1–2 | 0 | 0 | 1 | 0 | 0 | 0 | |
| | | 3 | 0 | 0 | 0 | 0 | 0 | 0 | 0 | | |
| PAK 2 | mixture of trichloro-N,N-di-sec.butyl-benzamides(2,3,6 Cl₃=75%; 2,3,5 Cl₃ = 25%) | 6 | 1 | 2–3 | 3–4 | 3 | 3 | 0 | 0 | 0 | |
| | | 3 | 0 | 2 | 3 | 2 | 1 | 0 | 0 | | |
| PAK 1 | mixture of monochloro-N,N-di-sec.butyl-benzamides (5 Cl=83.1%; 2Cl=14.1%; 4Cl=2%) | 6 | 0 | | 0 | 0 | 0 | 0 | 0 | 0 | |
| | | 3 | 0 | | 0 | 0 | 0 | 0 | 0 | | |
| PAK 3 | mixture of dichloro-N,N-di-sec.butyl-benzamides (2,5Cl₂= | 6 | 0 | | 0 | 0 | 0 | 0 | 0 | 0 | |

TABLE 2-continued

| | | | | | | | | |
|---|---|---|---|---|---|---|---|---|
| | 70%; 2,3-Cl$_2$=23%; 3,4-Cl$_2$=7%) | | | | | | | |
| PAK 4 | mixture of trichloro-N,N-di-sec.butyl-benzamides (2,4,5-Cl$_3$=66%; 2,3,4-Cl$_3$=33%) | 6 | 0 | 0 | 0 | 0 | 0 | 0 | 0 |

The following illustrates in more detail the range of the activity of PA 106, though, of course, the reported data are to be taken purely as a demonstrative example of the herbicidal activity of this product. It therefore must be considered as nonlimitative of the invention whose scope includes the use of this herbicide also against other weeds and other agricultural cultivations not listed herein, as well as particular procedures of treatment.

TABLE 3 reports data on the herbicidal activity against infesting herbs, while TABLE 4 reports data concerning the activity on useful species of agricultural cultivations. These tables employ the criterion explained previously. The product was spread on the soil one day after sowing, in quantities of 1, 3, 6, 8, 10, 12 and 14 kg/ha.

In the case of gladiolus, the treatment was carried out after unearthing the tubers.

Depending on the surrounding conditions and on the technical means available, preference may be given to one type of composition rather than to another.

Either solid or liquid compositions can be used. Solid compositions in the form of granules are prepared either by thoroughly mixing together the active substance with solid inert carriers such as: bentonite, calcium carbonate, vermiculite, attapulgite, pyrofillite, sepiolite, phosphorite, superphosphates, etc., or by spraying the active substance, dissolved in a volatile solvent, onto the granular carrier, mixing the whole and then drying the granules.

The contents in active substance may vary within wide limits, for instance between 0.25% and 80%, but preferably between 0.50% and 20%. The particle size of the granular carrier may vary from 0.1 mm to 4 mm, but preferably from 0.15 to 0.7 mm.

The granular compositions are among the preferred

TABLE 3

| Infesting species: | Doses in kg/ha: | | | | | | |
|---|---|---|---|---|---|---|---|
| | 1 | 3 | 6 | 8 | 10 | 12 | 14 |
| Panichum Dichotomi florum M. | 2 | 5/4 | 4 | 4 | 4 | 4 | 4 |
| Digitaria sanguinalis L. | 2/3 | 4/3 | 4 | 4 | 4 | 4 | 4 |
| Sorghum sp. | 1 | 3 | 4 | 4 | 4 | 4 | 4 |
| Enchinochola crus-galli R;S. | 0/1 | 3 | 4 | 4 | 4 | 4 | 4 |
| Setaria glauca L. | 2/3 | 3 | 4 | 4 | 4 | 4 | 4 |
| Papmer rhoeas L. | 0 | 1 | 2 | 3 | 4 | 4 | 4 |
| Amaranthus retroflexus L. | 0 | 1/2 | 3 | 4/3 | 4 | 4 | 4 |
| Chenopodium album L. | 0 | 1 | 3 | 2/3 | 3 | 5 | 3/4 |
| Artemisia vulgaris L. | 0 | 1 | 3 | 3 | 3 | 4/3 | 4 |
| Portulaca oleracea L. | 0 | 1/2 | 3 | 3/4 | 4 | 4 | 4 |

TABLE 4

| Agrarian species: | Doses in kg/ha: | | | | | | |
|---|---|---|---|---|---|---|---|
| | 1 | 3 | 6 | 8 | 10 | 12 | 14 |
| Phaseolus vulgaris L. (beans) | 0 | 0 | 0 | 0 | 0 | 0/1 | 0/1 |
| Pisum Sativum L. (peas) | 0 | 0 | 0 | 0 | 0 | 0 | 0 |
| Brassica oleracea, L. (cabbage) | 0 | 0 | 0/1 | 1 | 1/2 | 1/2 | 2 |
| Soja Hispida L. (soya) | 0 | 0 | 0 | 0 | 0/1 | 0/1 | 0/1 |
| Hordeum vulgare L. (barley) | 0 | 0 | 0 | 0 | 0/1 | 0/1 | 0/1 |
| Zea mais L. (corn) | 0 | 0 | 0 | 0 | 0 | 0/1 | 1 |
| Beta vulgaris L. (sugar beet) | 0 | 0 | 1 | 1 | 1/2 | 2 | 2/3 |
| Gladiolus sp. | 0 | 0 | 0 | 0 | 0 | 0 | 0 |
| Triticum vulgare (wheat) | 0 | 0 | 0 | 0/1 | 0/1 | 1 | 1 |
| Brassica napus L. colza) | 0 | 0 | 1 | 1/2 | 2/3 | 3 | 3 |
| Oryza sativa L. (rice) | 0 | 0 | 0 | 0 | 0 | 0 | 0/1 |
| Avena sativa L. (oats) | 0 | 0 | 0 | 0 | 0/1 | 0/1 | 1 |

The compounds according to this invention are either liquids or crystalline solids, generally slightly soluble or practically insoluble in water and soluble in common organic solvents. As is known, because of the necessity of distributing small quantities of active principles over large surface areas, the herbicide are not used as such in the herbicidal treatment but are used as compositions that contain them together with solid inert substances that act as carriers and as diluents or together with other substances that will facilitate their dispersion in a diluting medium such as water, before use.

compositions because their distribution on the soil can be carried out by use of equipment normally available on agricultural farms. Powdery compositions may be prepared by recourse to the abovementioned technique, using as a carrier calcium phosphate, calcium carbonate, kaolin, bentonite, Fuller's earth, talc, pyrofillite, calcium silicate, superphosphate, etc., by grinding the coarse powders until attaining the desired fineness.

The so-called "wettable powders" are obtained by incorporating one or more surfactant agents into the powders. By dispersing these wettable powders in water, it is possible to obtain aqueous suspensions at the desired concentrations in active substance. These aqueous dispersions are sprayed onto the soil.

Liquid emulsifiable compositions are prepared by dissolving the active substance in an inert solvent, preferably slightly soluble in water, such as for instance benzene, toluene, and by adding a surfactant agent.

When these compositions are added to water, emulsions are obtained in which the solvent phase is dispersed in the aqueous phase while the active substance is maintained dissolved in the dispersed phase. In this way a uniform distribution is obtained of the active substance in the aqueous composition which is sprayed onto the soil.

In the preparation of wettable powders and of emulsifiable concentrates, emulsifying-dispersing agents of the anionic, nonionic or cationic type may be used. Among the agents of the anionic type may be listed: sodium dodecyl-benzene-sulphonate, calcium naphthalene-sulphonate, laurylsulphate; of the active cationic type quaternary ammonium compounds may be used, such as: cetylpyridinium-bromide, dodecylbenzylmethylammonium chloride, di-(hydroxyethyl)-benzyl-dodecylammonium chloride; among the nonionic agents are: condensation products of ethylene oxide with aliphatic alcohols, amines, fatty acids, alkylphenols. All of the above compounds are readily commercially available.

The preparation of compositions of any type containing compounds of this invention presents no difficulties as they can be prepared easily by making use of the known techniques. If desired, herbicides with a complementary algacidal activity or pesticides, fertilizers, etc. may be incorporated into these compositions. The use of any type of composition, independently from the techniques followed in the herbicidal treatment, falls within the scope of this invention.

Among the preferred types of composition we cite hereinbelow for illustrative but not limiting purposes just a few:

Granulate: PA 106 5%, 1% sodium di-iso-octylsulphosuccinate, 94% bentonite in granules with a φ (diameter) for 80% between 1 and 0.5 mm. It is prepared by suitably dissolving 5 parts of PA 106 + 1 part of sodium di-iso-octylsulphosuccinate in 1 part methylene chloride, and by then spraying the solution onto the granular carrier until attaining complete absorption. The solvent is then removed by evaporation and is then recovered.

Granulate: PA 106 5%, sepiolite 95% in granules of a diameter comprised, as an average, between 0.5 and 0.25 mm. The mixture is prepared either by directly mixing or by spraying onto the granular carrier the active substance dissolved in a solvent.

Emulsifiable oil: PA 106 50%, xylene 30%, Soprofor NPA 20% (oxyethylated and sulphonated fat). It is prepared by directly mixing the compounds under shaking.

Emulsifiable oil: PA 106 50%, xylene 40%, Atlox 5848 6%, Atlox 8916P 4% (derivatives from polyoxymethylene sorbitanesters of fatty acids and their resinous derivatives in admixture with alkylarylsulphonates). It is prepared by directly mixing the components under shaking.

The quantities that are used in the herbicidal treatment vary considerably in relation to the contents in active principle, to the species of the plants, and to the treatment technique. In general these quantities must be such as to supply from 1 – 10 kg of active principles per hectar of soil. We have, for instance, used with much success granular compositions containing 5% of compound or compounds according to the invention in the selective herbicidal treatment to remove from rice the Echinocloa crus-galli and from Panicum dichotoniflorum, infesting gramineae predominant in rice fields, in such quantitites of compositions as to supply to the soil 2 – 10 kg of active principles. In this case the pronounced selective action of the products according to this invention with regard to these infesting plants is exploited.

It is quite known to the man skilled in the art that the herbicidal treatment of rice involves particular difficulties both with respect to the close botanical affinity of the weeds with the useful plants, as well as with respect to the particular surrounding conditions of rice growing.

As is known, the inhibition of growth of those infestants may be carried out either in post-emergence or in pre-emergence. In this latter case the herbicide must exert its action on a submerged or flooded field, since the chambers of the rice fields are flooded immediately after sowing; the herbicide must, therefore, possess particular characteristics besides the selective action, that is, it must have a persistent action in this particular environment, it must be non-volatile, it must be very little soluble in water in consideration of the fact that in the areas of the rice fields there is a continuous renewal of water and the out-flowing or downstream water may reach other existing cultivations or it may be used for irrigation or other like purposes. The herbicide must therefore remain uniformly distributed on the soil also under these particular conditions and it must exert its action for long stretches of time.

It is extremely difficult to find combined in the same single product with a herbicidal action all these characteristics.

We have found that compounds comprised by the general formula (I), have the required requisites for being used by the farmers to their full satisfaction in this particular field of application.

The development of the species indicated above is practically inhibited when the small plant is in the "sprouting" stage. The herbicidal treatment may be carried out either before sowing or after the sowing. In any case one obtains the permanent stopping of the vegetative development and the subsequent death of the infesting plants, while the rice remains completely unharmed. This is a further aspect of the invention which is of great technical and economical importance which will be illustrated in the following by some examples of a non-limiting character.

EXAMPLE No. 1

A series of pots were prepared filled with rice-field earth. Into these were then sown Echinocloa crus-galli and rice. The earth was then submerged by 10 cm of water and immediately thereafter were uniformly spread on the submerged soil granular compositions, some of them containing 2% of PA 234 and 98% of phosphorite, some others 5% of PA 234 and 95% of bentonite, in doses graduated from 0 – 8 kg of active principle per hectar. The test pots were kept in a conditioned environment at controlled temperature and photo-period.

It was ascertained that under a 3 kg/ha dose of active principle, the growth of the Echinocloa crus-galli was totally inhibited, while the rice, even under the maximum dose, remained undamaged.

EXAMPLE No. 2

Into 2 sq.m. basins containing rice-field soil were sown rice and Echinocloa crus-galli. After having submerged the soil with 10 cm of water, treatments were carried out by distributing uniformly on the soil a granular composition containing 5% of PA 300 and 95% of bentonite in doses equal to 0 - 4 - 6 - 8 kg of active principle per hectar. Following periodical observations it was ascertained that the rice developed regularly in all basins except in the control basin, where its development was hindered by the competing growth of Echinocloa crus-galli. In the treated basins, no Echinocloa crus-galli plant developed while in the control basin the growth of the infesting plant was vigorous, equal to 33 plants of Echinocloa crus-galli per sq.m.

EXAMPLE No. 3

In this test a granular composition of PA 106 containing 5% of active principle and 95% of bentonite was used. The treatment was carried out in a rice field with areas of from 900 to 1000 sq.m on naked soil flooded just shortly before the sowing of the rice. There were used doses of granulate equal to 4, 6, 8 and 10 kg of active substance per hectar of surface. It was ascertained that while in the non-treated areas the degree of infestation by Echinocloa crus-galli was considerable, equal to 2500 plants per area, and the development of the rice had been hindered by the competing growth of the infestant, in the areas treated with 6 kg of PA 106, the inhibition of growth of the infestant could for all practical purposes be considered as total. The rice in all the treated areas had grown vigorously, without suffering any damage even by greater doses of herbicide applied.

In a subsequent plot-test conducted in open field on areas of 80 sq.m planted with rice, when using a granular composition containing 5% of PA 106 and 95% of bentonite at different growing doses, no phytotoxic effects on the rice could be observed even at a dose of 30 kg/ha of active substance.

The following are a few examples of the preparation of compounds according to this invention and of two N-sec.butyl-N-alkylamines not known to the literature.

Preparation of 3-bromo-N,N-di-sec.butyl-benzamide:

Into a 150 ml flask, provided with a reflux condenser, were introduced 10 g of 3-bromo-benzoyl chloride dissolved in 25 ml of anhydrous $C_6H_6$ and a solution of 6 g of di-sec.butylamine in 10 ml of anhydrous $C_6H_6$ and 4.9 g of triethylamine. The whole was then heated to reflux temperature for about 1 hour. The mass was thereupon permitted to cool down to room temperature and the solvent was then removed under a reduced pressure. The mixture was then washed with acidulated $H_2O$, with $H_2O$ and then extracted with ethyl ether. The etheric extract was dried on anhydrous $Na_2SO_4$, filtered and the solvent removed under reduced pressure. The oily residue was subjected to fractional distillation at 0.05 mm Hg and the fraction passing over at 153°–154°C was collected. Obtained thereby was 14.7 g of distillate consisting of 3-bromo-N,N-di-sec.butyl-benzamide.

The analysis gave: calculated C = 57.70%, found C = 57.79%; calculated H = 7.10%, found H = 7.28%.

Preparation of 3,5-dichloro-N,N-di-sec.butyl-benzamide

Into a 2,000 ml three-necked flask, cooled externally with ice, were introduced 100 g of dry and well powdered anthranylic acid, suspended in 400 ml of anhydrous benzene. Through a separatory funnel a solution of 100 ml of $SO_2Cl_2$ in 200 ml of anhydrous benzene was added to the mass, under vigorous stirring. The addition is carried out in a stretch of time of about 1 hour. The suspension was boiled to reflux temperature for 5 hours, still under stirring. During this operation a strong development of HCl was observed. The mass was then cooled, diluted with an equal volume of ligroin, permitted to stand at 0°C for 1 hour and was finally filtered and washed with ligroin. The precipitate, after drying, was treated with 1500 ml of hydrochloric acid at 8%, under constant stirring and heating up to 50°–60°C. The whole was then filtered thereby obtaining an insoluble fraction consisting of about 50 g of raw 3,5-dichloroanthranyl acid (melting point 200°–230°C). After crystallization from ethanol/$H_2O$ about 38 g of 3,5-dichloroanthranyl acid with a melting point of from 230° to 231°C were obtained.

10 g of 3,5-dichloroanthranyl acid were then dissolved, by adding it in small portions at room temperature and under stirring, in 75 ml of concentrated $H_2SO_4$. The whole was then cooled down and, keeping the temperature at 0°C, and 7.5 g of $NaNO_2$ was added thereto under vigorous stirring, in small doses. On completion of the addition, the stirring was continued for another two hours, still maintaining the temperature at 0°C. The mass was then poured in a thin flow into ice and was filtered, being careful that the mass did not exceed 0°C (one operates always in the presence of ice).

The solution thus obtained was then added in small doses to a double volume of boiling ethanol, keeping the whole under stirring. Once the development of nitrogen had stopped, the whole was cooled down, diluted with $H_2O$ and, after 2 hours at 0°C, was filtered by washing with $H_2O$. 7 g of raw product with a melting point of from 184°–187°C were obtained thereby. The product was then crystallized from ethanol/$H_2O$.

Into a 150 ml flask, provided with a reflux condenser, were introduced 7 g of 3,5-dichloro-benzoic acid and 20 g of $SOCl_2$ and the whole was then reflux heated for about 1 hour. Thereupon the excess of $SOCl_2$ was removed under reduced pressure in a rotating evaporator. The oil that remained, after purification by fractional distillation, was treated with anhydrous $C_6H_6$. Added to this was a solution of 4.5 g of di-sec.butylamine in 10 cc of anhydrous $C_6H_6$ and 3.7 g of triethylamine. The whole was then heated to reflux temperature for about 1 hour. Thereupon, the mass was left to cool down to room temperature and the solvent was removed under reduced pressure. The mass remaining was then washed with acidulated $H_2O$, with $H_2O$ and finally extracted with ethyl ether. The ether extract was then dried on anhydrous $Na_2SO_4$, filtered and the solvent removed under reduced pressure. 9.9 g of white-yellow crystals consisting of 3,5-dichloro-N,N-di-sec.-butyl-benzamide were obtained.

The mass was then dissolved in a minimum quantity of boiling $C_2H_5OH$ and then cooled down to 0°C. Thus 8.9 g of white crystals showing a melting point of from 122° to 123°C were obtained.

The analysis gave: calculated C = 59.61%, found C = 59.86%; calculated H = 7.00%, found H = 7.03%.

Preparation of 3,4-dichloro-N-sec.butyl,N-n.butyl-benzamide

Into a 250 ml flask provided with a reflux condenser, were introduced 24.9 g of 3,4-dichlorobenzoyl chloride dissolved in 30 ml of anhydrous $C_6H_6$, a solution of 15.3 g of N-sec.butyl-N,n-butylamine in 20 ml of anhydrous $C_6H_6$ and 13.1 g of triethylamine. This mass was heated to reflux temperature for about 1 hour. The whole was then cooled down to room temperature and the solvent was removed under reduced pressure in a rotating evaporator. The mass was then washed with acidulated $H_2O$, with $H_2O$ and was extracted with ethyl ether. The ether extract was then dried on anhydrous $Na_2SO_4$, filtered and the solvent removed under reduced pressure in a rotating evaporator. The oily residue was subjected to fractional distillation at 0.02 mm Hg and the fraction passing over at 139°–140°C was collected. 30.5 g of distillate constituted by 3,4-dichloro-N-sec.-butyl,N,n.butyl-benzamide were obtained.

The analysis gave: calculated C = 59.61%, found C = 59.44%; calculated H = 7.00%, found H = 6.86%.

Preparation of 2,3,5-trichloro-N,N-di-sec.butyl-benzamide

The acid was prepared according to the known technique, more particularly according to Cohen J. B., Dakin H. D. Soc. 81, 1331 (1902).

Into a 250 ml flask, provided with a reflux condenser, were introduced 10 g of 2,3,5-trichlorobenzoyl chloride in 20 ml of anhydrous $C_6H_6$, a solution of 5.3 g of di-sec.butylamine in 7 ml of anhydrous $C_6H_6$ and 5 g of triethylamine. This mass was then heated to reflux temperature for about 1 hour. Thereupon it was left to cool down to room temperature and the solvent was removed under reduced pressure in a rotating evaporator. The mass was then washed with acidulated $H_2O$, with $H_2O$ and was then extracted with ethyl ether. The etheric extract was then dried on anhydrous $Na_2SO_4$, filtered and the solvent removed under reduced pressure. 12.6 g of yellowing crystals of 2,3,5-trichloro-N,N-di-sec.butyl-benzamide were obtained.

The crystalline mass was thereupon dissolved in the minimum quantity of boiling $C_2H_5OH$ and cooled down to 0°C. Thereby were obtained 11.5 g of white crystals having a melting point of 111°–112°C.

The analysis gave: calculated C = 53.15%, found C = 53.52%; calculated H = 5.99%, found H = 5.88%; calculated Cl = 31.59%, found Cl = 31.56%.

Preparation of 3-chloro,4-methyl-N,N-di-sec.butyl-benzamide

Into a 150 ml flask, provided with a reflux condenser, were placed 17.1 g of 3-chloro-4-methyl-benzoic acid (prepared according to French Pat. No. 835,727) and 55.5 g of $SOCl_2$ and the whole was heated to reflux until complete dissolution. The boiling was continued for another 30 minutes. The excess in $SOCl_2$ was then removed under vacuum and the residue was subjected to fractional distillation at a pressure of 0.2 mm Hg. The fraction passing over at 95°C was then collected. 17.9 g of the chloride of 3-chloro,4-methylbenzoic acid were obtained.

To these 17.9 g of the chloride of 3-chloro,4-methyl-benzoic acid, dissolved in 60 ml of anhydrous benzene, were added 12.9 g of di-sec.butylamine dissolved in 15 ml of anhydrous $C_6H_6$ and 12.3 g of triethylamine. The whole was then boiled to reflux temperature for 1 hour and was then left to cool down to room temperature. The reaction mass was then concentrated to dryness under reduced pressure. The residue was washed with acidulated $H_2O$, with $H_2O$ and extracted with ethyl ether. The etheral extract was dried on anhydrous $Na_2SO_4$, filtered, and the solvent was then removed by reduced pressure. The oily residue was fractionally distilled at a pressure of 0.05 mm Hg. The fraction which passed over at 143°–144°C was collected. Thereby were obtained 26.5 g of 3-chloro,4-methyl-N,N-di-sec.butyl-benzamide.

The analysis gave: calculated C = 68.19%, found C = 64.93%; calculated H = 8.55%, found H = 8.83%.

The two unknown asymmetric amines which are used for preparing the compounds according to the invention, have been synthesized in the following manner.

Preparation of N-sec.butyl,N-sec.amylamine

Into a 150 ml flask, provided with a reflux condenser, were placed 14.6 g of monosec.butylamine dissolved in 15.5 ml of $C_2H_5OH$. Added thereto was 30 g of 2-bromo-pentane. This mass was then boiled to reflux temperature for 10-12 hours and thereafter cooled down and neutralized with dilute $H_2SO_4$. The whole was then evaporated to dryness. The residue thus obtained was treated with an excess of a 15% NaOH solution and extracted with 3 successive portions of ethyl ether. The ether extracts were then combined and washed with $H_2O$, dried or anhydrous $Na_2SO_4$, filtered and the ether removed by evaporation. The residue was distilled under atmospheric pressure and the fraction was gathered which passed over at 160°–161°C. 15.75 g of N-sec.butyl,N-sec.amylamine were obtained thereby. The picrate shows a melting point of from 61°–63°C (crystals from petroleum ether). The analysis of the picrate gave: calculated C = 48.58%, found C = 48.22%; calculated H = 6.50%, found H = 6.4%.

By operating as hereinabove described and by using 2-bromopropane as an alkylating substance for the mono-sec.butylamine, it is possible to obtain N-iso-propyl-N-sec.butylamine with a boiling point of 112°–114°C (at 760 mm Hg); and the chlorohydrate with m.p. = 139°–140°C (crystals from ethanol-ether).

The analysis of the chlorohydrate gave: calculated C = 55.45%, found C = 55.41%; calculated H = 11.96%, found H = 11.97%; calculated Cl = 23.47%, found Cl = 23.38%.

Hereunder are given several data relating to the toxicity towards warm-blooded animals of some products according to the invention.

| Mark | Product | LD 50 per os on rat mg/kg |
|---|---|---|
| PA 484 | 3,4-dibromo-N,N-di-sec.butyl-benzamide | 2.550 |
| PA 489 | 3,bromo-4,chloro-N,N-di-sec.butyl-benzamide | 2.500 |
| PA 631 | 3,4-dichloro-N,N-di-sec.butyl-benzamide | 930 |
| PA 300 | 2,3,5-trichloro-N,N-di-sec.butyl-benzamide | 2.000 |

-continued

| Mark | Product | LD 50 per os on rat mg/kg |
|---|---|---|
| PA 234 | 3,5-dichloro-N,N-di-sec.butyl-benzamide | 2.000 |
| PA 106 | 3,4-dichloro-N,N-di-sec.butyl-benzamide | 1.450 |

We claim:

1. A composition for selectively inhibiting the growth of undesirable plants infesting soil planted with agrarian cultures, said composition containing an effective amount of a mixture of dichloro-:N,N-di-sec.butylbenzamide, containing 70% of 2,5-dichloro, 23% of 2,3-dichloro and 7% 3,4-dichloro and an inert carrier.

2. A composition for selectively inhibiting the growth of undesirable plants infesting soil planted with agrarian cultures, said composition containing an effective amount of a mixture of trichloro-N,N-di-sec.butyl benzamide, containing 75% of 2,3,6-trichloro and 25% of 2,3,5-trichloro and an inert carrier.

3. A composition for selectively inhibiting the growth of undesirable plants infesting soil planted with agrarian cultures, said composition containing an effective amount of a mixture of trichloro-N,N-di-sec.butyl-benzamide, containing 66% of 2,4,5-trichloro and 33% of 2,3,4-trichloro and an inert carrier.

4. Method of selectively inhibiting the growth of undesirable plants infesting soil planted with agrarian cultures which comprises applying to the said soil an effective amount of compound having the formula:

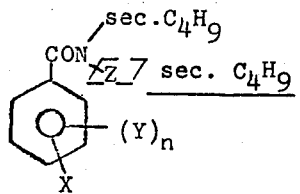

wherein:
X = Cl, Br, I, $CH_3$;
Y = H, Cl, Br, I, F, $CH_3$;
n = 1 or 2,
and when n is 2, only one of X and Y may be $CH_3$.

5. Method of selectively inhibiting the growth of undesirable plants infesting rice fields which comprises applying to the said rice field an effective amount of compound having the formula:

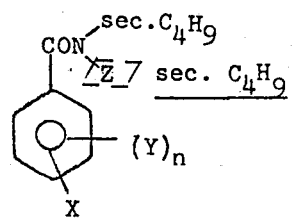

wherein:
X = Cl, Br, I, $CH_3$;
Y = H, Cl, Br, I, F, $CH_3$;
n = 1 or 2,
and when n is 2, only one of X and Y may be $CH_3$.

6. A method as claimed in claim 4 wherein a composition which contains at least one compound of said formula and a carrier therefor is applied to the said soil.

7. A method as claimed in claim 5 wherein a composition which contains at least one compound of said formula and a carrier therefor is applied to said rice field.

* * * * *